United States Patent [19]
Cocito

[11] Patent Number: 4,711,587
[45] Date of Patent: Dec. 8, 1987

[54] METHOD OF AND APPARATUS FOR MEASURING THE SOFTENING POINT OF A VITREOUS SPECIMEN

[75] Inventor: Giuseppe Cocito, S. Giusto Can.se, Italy

[73] Assignee: Cselt-Centro Studi e Laboratori Telecomunicazioni S.p.A., Turin, Italy

[21] Appl. No.: 887,275

[22] Filed: Jul. 21, 1986

[30] Foreign Application Priority Data

Jul. 24, 1985 [IT] Italy ............................... 67676 A/85

[51] Int. Cl.4 ............................................. G01N 25/04
[52] U.S. Cl. ....................................... 374/16; 374/46; 73/847
[58] Field of Search ....................... 374/16, 22, 23, 46, 374/25, 48, 160; 73/847

[56] References Cited

U.S. PATENT DOCUMENTS

| 2,579,424 | 12/1951 | Gehman | 374/46 |
| 2,856,769 | 10/1958 | Bennett et al. | 73/847 |
| 3,277,700 | 10/1966 | Myerholtz, Jr. | 374/48 |
| 3,369,391 | 2/1968 | Warfield | 374/16 |
| 3,380,291 | 4/1968 | Wilson | 374/46 |
| 3,696,664 | 10/1972 | Moser et al. | 73/847 |
| 3,718,028 | 2/1973 | Moser et al. | 374/48 |
| 3,756,074 | 9/1973 | Hedvig | 374/48 |
| 4,259,860 | 4/1981 | Labino | 374/23 |

FOREIGN PATENT DOCUMENTS

| 0114437 | 7/1984 | Japan | 73/847 |
| 1334455 | 10/1973 | United Kingdom | 374/16 |
| 0185536 | 8/1966 | U.S.S.R. | 374/46 |
| 0192473 | 2/1967 | U.S.S.R. | 374/46 |
| 0930064 | 5/1982 | U.S.S.R. | 374/46 |

Primary Examiner—Charles Frankfort
Assistant Examiner—Thomas B. Will
Attorney, Agent, or Firm—Karl F. Ross; Herbert Dubno

[57] ABSTRACT

A method of and an apparatus for measuring the softening point of a vitreous specimen in which the viscosity variation as a temperature function is determined by applying torsion to the specimen and measuring the transmitted torque as a function of temperature.

6 Claims, 1 Drawing Figure

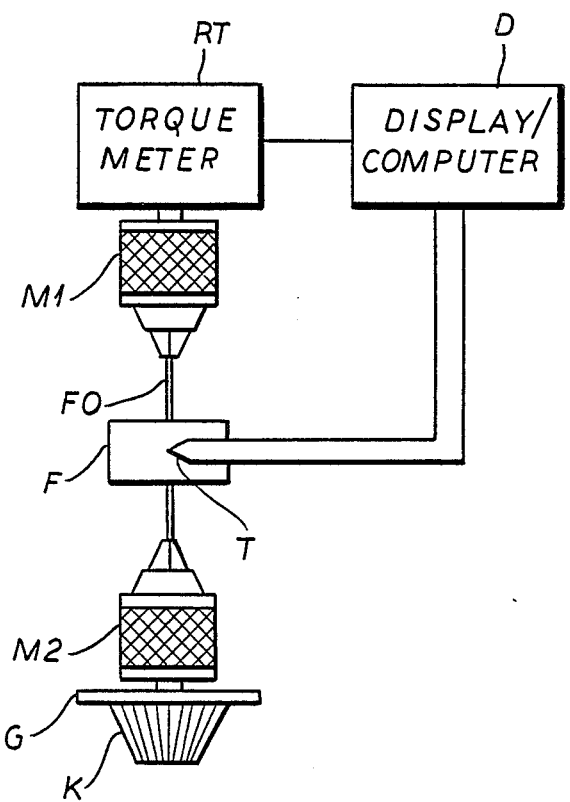

METHOD OF AND APPARATUS FOR MEASURING THE SOFTENING POINT OF A VITREOUS SPECIMEN

FIELD OF THE INVENTION

My present invention relates to a method of determining the softening point of a vitreous material and, more particularly to a method of and to an apparatus for measuring the softening point of a specimen made from a vitreous material, e.g. a glass fiber.

BACKGROUND OF THE INVENTION

The characterization of vitreous materials and articles made therefrom, e.g. glass fibers, for example optical fibers for use in communication, requires the knowledge of various parameters of the material including the softening point.

The softening point of a vitreous material can be defined as the temperature at which the material attains a viscosity level at which it can no longer be considered a solid.

Generally speaking vitreous material cannot be considered to have a change of state from the solid to a liquid at a single well-defined temperature. Consequently, one refers to the temperature range at which the viscosity drops from a high viscosity to a low viscosity as a softening point.

In the viscosity-temperature plane, there is a first viscosity zone, a second low-viscosity zone and a third zone comprising the softening point located between them.

In the fabrication and handling of optical fibers, the softening point must be determined in order to evaluate the possibility of carrying out operations such as the fabrication of the so-called fusion splices, i.e. connections between two optical fibers effected by heating the ends to be joined to the softening point and then bringing them together.

Where the fibers are composed of different materials, a disparity in their softening points may pose a significant problem. In such cases fiber compatibility is poor and residual stresses remain in the fusion zone which is very fragile.

One apparatus for determining the softening point of a glass fiber is described in TutorialSymposium Proceedings, New York, 8-9 June 1970, pages 355-357.

A cylinder or rod of a given length of the glass to be measured is suspended in a furnace and its increase in length as function of temperature is determined by suitable detectors.

The temperature is increased in accordance with a particular law and the softening point is determined as the temperature at which the lengthening rate of the fiber attains a predetermined value. This apparatus is characterized by low reproducibility. When the test specimen reaches the softening point, it begins to lengthen, but also its cross section decreases and surface strains and the rate of increase in temperature play a role. Density and surface tension of the test glass also play a role. The results are, therefore, not always reliable and are seldom reproducible, especially for higher temperatures and greater decrease of the lengthening rate.

OBJECTS OF THE INVENTION

It is the principal object of the present invention to provide an improved method of determining a softening point of a vitreous specimen whereby these drawbacks are avoided and the measurement is more reliable and highly reproducible.

A more specific object of the invention is to provide a method and apparatus for the purposes described and which allow accurate detection of the viscosity curve as a function of temperature without involving deformation of the test specimen and which enables the technique to be used with both increasing and decreasing temperature. Moreover, the proposed method is independent from density and less dependent upon surface tension of the test glass.

SUMMARY OF THE INVENTION

These objects and others which will become apparent hereinafter are attained in a method of measuring the softening point of a vitreous specimen in which the viscosity changes of the specimen under temperature variations are detected and which is characterized by the fact that the specimen is subjected to torsion and the torque variations are recorded as a function of temperature, the softening point being found as the temperature interval in which the viscosity drops.

More specifically the invention provides a method of determining the softening point of a vitreous specimen, comprising the steps of:

(a) imparting torsion to the specimen;

(b) heating a portion of the specimen over a temperatur range including the softening point of the specimen and measuring the temperature to which the specimen is heated;

(c) measuring torque developed by the specimen, the torque varying with the temperature to which the specimen is heated as a function of viscosity changes in the specimen; and;

(d) obtaining from the measured torque with respect to temperature, the softening point in the temperature interval in which the viscosity drops.

Advantageously the specimen is a glass fiber and the torsion is imparted to the fiber by applying a twist of a given angle to one end of the fiber, the torque is measured by detecting the torque at an opposite end of the fiber, and the specimen is heated by passing the fiber through a furnace while measuring the temperature of the fiber in the furnace.

The apparatus for determining the softening point of a vitreous specimen can comprise:

(a) means for imparting torsion to the specimen;

(b) means for heating the specimen over a temperature range including the softening point of the specimen and measuring the temperature to which the specimen is heated;

(c) means for measuring torque developed by the specimen, the torque varying with the temperature to which the specimen is heated as a function of viscosity changes in the specimen; and;

(d) means for obtaining from the measured torque with respect to temperature, the softening point in the temperature interval in which the viscosity drops.

When the specimen is a glass fiber or rod, the means for imparting torsion to the specimen can include chuck engaging one end of the fiber and a protractor for angularly displacing the chuck and locking same at a predetermined angle.

The means for measuring torque developed by the specimen can include another chuck clamping an opposite end of the fiber and a torque meter operatively connected with the other chuck and responsive to twist imparted thereto by the fiber. In another obvious configuration, one chuck is maintained in a fixed position, the other chuck includes means both for imparting torsion and measuring torque.

The means for heating the specimen over a temperature range can include the softening point of the specimen and measuring the temperature to which the specimen is heated includes a furnace traversed by only a portion of the length of the fiber between the chucks and provided with a thermometric probe.

BRIEF DESCRIPTION OF THE DRAWING

The above and other objects, features and advantages of the present invention will become more readily apparent from the following description, reference being made to the accompanying drawing in which the sole FIGURE is a diagrammatic elevational view of an apparatus for carrying out the method of this invention.

SPECIFIC DESCRIPTION

The apparatus for carrying out the invention comprises a torque meter RT which can be connected to a display D which can include a computer calculating the temperature interval of the maximum rate of viscosity drop and receiving an input as well from a thermometric device T measuring the temperature of the specimen FO and providing its temperature input to the display/computer D.

The optical fiber FO is clamped in a chuck or mandrel M1 connected to the torque meter RT.

A second chuck or mandrel M2 clamps the opposite end of the fiber or rod and has protractor G which can be rotated by a knob K and locked in selected angular positions to apply varying but predetermined degrees of torque to the fiber FO.

The optical fiber FO traverses a small size furnace F which can raise the temperature of the fiber up to about 1800° C. and is equipped with the thermometric probe T previously mentioned.

To effect the measurement, the unclad fiber FO is clamped between the two chucks M1, M2 and is twisted to an angle which may be selected as a function of the diameter and structure of the fiber, although this angle is not critical as long as it applies a measurable torque to the fiber as detected at the torque meter RT.

The furnace is switched on and the temperature and torque are plotted versus time, the recording being repeated passing from high to low temperature values. Where the inflection points of the two temperature versus torque plots coincide can be selected as the softening point, i.e. the softening point is located exactly in the interval of the viscosity drop.

With a suitable selection of the torsion angle, the deformation of the fiber can be limited as desired although the results remain reliable over a wide temperature range.

Naturally the device illustrated can be modified, for example, to adapt the chucks to the configurations of various specimens to be tested. So, as previously stated, one of the mandrels can contain both the torque meter RT and the rotator to apply angular torsion to the fiber specimen, whereby the other mandrel is fixed.

The apparatus is particularly suitable for total automation and, for instance, the rotation of the chuck M2 and the heating can also be automatically controlled by the computer, which can include a programmed microprocessor so as to automatically extract curve families fully representing the softening phenomena of the vitreous material.

I claim:

1. A method of determining the softening point of a vitreous specimen, comprising the steps of:
   (a) imparting torsion to said specimen;
   (b) heating a portion of said specimen over a temperature range including the softening point of the specimen and measuring the temperature to which said specimen is heated;
   (c) measuring torque developed by said specimen, said torque varying with the temperature to which said specimen is heated as a function of viscosity changes in said specimen; and;
   (d) obtaining from the measured torque with respect to temperature, the softening point in the temperature interval in which said viscosity drops.

2. The method defined in claim 1 wherein said specimen is a glass fiber and the torsion is imparted to said fiber by applying a twist of a given angle to one end of the fiber, the torque is measured by detecting the torque at an opposite end of the fiber, and the specimen is heated by passing the fiber through a furnace while measuring the temperature of the fiber in the furnace.

3. An apparatus for determining the softening point of a vitreous specimen, comprising:
   (a) means for imparting torsion to said specimen;
   (b) means for heating said specimen over a temperature range including the softening point of the specimen and measuring the temperature to which said specimen is heated;
   (c) means for measuring torque developed by said specimen, said torque varying with the temperature to which said specimen is heated as a function of viscosity changes in said specimen; and;
   (d) means for obtaining from the measured torque with respect to temperature, the softening point in the temperature interval in which said viscosity drops.

4. The apparatus defined in claim 3 wherein said specimen is a glass fiber, and said means for imparting torsion to said specimen includes a chuck engaging one end of said fiber and a protractor for angularly displacing said chuck and locking same at a predetermined angle.

5. The apparatus defined in claim 4 wherein said means for measuring torque developed by said specimen includes another chuck clamping an opposite end of said fiber and a torque meter operatively connected with said other chuck and responsive to twist imparted thereto by said fiber.

6. The apparatus defined in claim 5 wherein said means for heating said specimen over a temperature range including the softening point of the specimen and measuring the temperature to which said specimen is heated includes a furnace traversed by only a portion of the length of said fiber between said chucks and provided with a thermometric probe.

* * * * *